United States Patent [19]

Wilson

[11] 4,398,545
[45] Aug. 16, 1983

[54] PAIN-BLOCKING BANDAGE

[75] Inventor: J. A. Sam Wilson, Miami, Fla.

[73] Assignee: Cyclotechnical Medical Industries, Inc., Miami, Fla.

[21] Appl. No.: 274,302

[22] Filed: Jun. 16, 1981

Related U.S. Application Data

[63] Continuation-in-part of Ser. No. 83,388, Oct. 10, 1979, abandoned.

[51] Int. Cl.³ .............................................. A61N 1/36
[52] U.S. Cl. .................................. 128/798; 128/803; 128/421
[58] Field of Search .................... 128/783, 791–793, 128/798, 799, 802, 803, 379–381, 383, 384, 389, 390, 391, 420–423, 640, 207.21; 604/20

[56] References Cited

U.S. PATENT DOCUMENTS

| | | | |
|---|---|---|---|
| 770,014 | 9/1904 | Linn | 128/207.21 |
| 2,590,876 | 4/1952 | Landauer | 128/798 |
| 2,784,715 | 3/1957 | Kestler | 128/207.21 |
| 3,472,233 | 10/1969 | Sarbacher | 128/783 X |
| 3,480,010 | 11/1969 | Crossky | 128/419 R |
| 3,889,163 | 6/1975 | Symmes | 128/419 R |
| 3,911,910 | 10/1975 | Ocsau | 128/419 R |
| 4,051,842 | 10/1977 | Hazel et al. | 128/640 |
| 4,067,342 | 1/1978 | Burton | 128/798 |
| 4,082,087 | 4/1978 | Howson | 128/640 |
| 4,177,817 | 12/1979 | Bevilacqua | 128/802 |
| 4,325,367 | 4/1982 | Tapper | 128/207.21 |

FOREIGN PATENT DOCUMENTS

| | | | |
|---|---|---|---|
| 2342082 | 9/1977 | France | 128/421 |
| 410009 | 5/1934 | United Kingdom | 128/207.21 |

*Primary Examiner*—Lee S. Cohen
*Attorney, Agent, or Firm*—Donald A. Kaul

[57] ABSTRACT

A bandage to be applied adjacent to an injured portion of a patient's body contains electronic circuitry which delivers electric pulses into the body to block or mask the pain arising from the injury. The bandage includes an inner unit adapted to be applied directly onto the patient's skin and an outer unit adapted to be removably applied upon the inner unit. The inner unit includes spaced apart conductive portions which contact the patient's skin. The outer unit includes a power source and an electronic circuit which applies a voltage output to the conductive portions of the inner unit. The voltage output is transmitted through the conductive portions to the patient's skin to cause low current electrical pulses within the patient's body to block or mask the pain arising from the injury.

31 Claims, 25 Drawing Figures

PAIN-BLOCKING BANDAGE

This application is a continuation-in-part of application Ser. No. 06/083,388, filed Oct. 10, 1979, now abandoned.

This invention relates to a pain-blocking bandage which can be applied adjacent to the injured portion of a patient's body and which blocks or masks the pain arising from the injury. More specifically, this invention relates to a novel, flexible, self-contained bandage which utilizes electrical energy to create pulsing pain-blocking low electrical currents in the patient's body.

The concept of utilizing electrical energy applied to the human body for therapeutic purposes is extremely old and well known. History records that as early as 46 A.D., the Romans used electrical torpedo fish for the treatment of arthritis, headache and gout. Throughout the centuries following, various medical researchers have used electrical energy and electrical stimulation of the body for therapeutic, curative, and other purposes.

In more recent times, experimentation with the application of electrical energy to the human body has lead to the discovery of an unexpected and beneficial attribute, namely, the treatment of pain. Without discussing this attribute in great detail, since detailed discussions are set forth in available medical literature, it can be generally stated that the treatment of pain by electrical stimulation falls into an area known as transcutaneous electrical neuro-stimulation, also known as TNS or TENS. With the use of these techniques, it has been found that the electrical currents somehow block or mask the transmission of pain signals by the peripheral nervous system and through the central nervous system to the brain. As a result, even though the condition which causes the pain might still remain, the patient is greatly relieved because the sensation of pain is alleviated.

Many of the advances in the field of electrical stimulation of the human body have arisen since the year 1965 when Melzack and Wall published an article entitled "Pain Mechanisms: A New Theory" relating to the "gate" theory of pain. A subsequent article by Wall and Sweet entitled "Temporary Abolition of Pain In Man" demonstrated that stimulation of the primary afferent neuron led to pain relief. While certain aspects of the "gate" theory are now considered questionable, the mere publication of these articles encouraged a renewal of interest in the whole field of electrical stimulation and led to awakened research by many different individuals, companies, hospitals, and research institutions. As an outgrowth of this awakened research, new types of apparatus have been devised, developed and marketed for the purpose of delivering electrical stimulation to portions of the human body.

The apparatus which has been developed to take advantage of the discoveries relating to electrical stimulation of the body has essentially been of two general types. One type is the rather large, expensive, stationary machines which are installed in a building, such as a research institution or a doctor's office, where the patient must visit the location of the machine and be connected to the machine to receive treatment. The other type is the portable unit, usually of the TENS type, which includes a small body-carried, battery operated unit having a pair of electrodes connected by leads to the unit. The unit itself is carried by the patient, for instance, by attachment to the patient's belt, and the electrodes are then applied to different portions of the user's body. An example of this type of unit is disclosed in U.S. Pat. No. 4,017,347, issued Mar. 29, 1977.

While these known forms of apparatus have indeed represented medical advances, there are nevertheless certain drawbacks and deficiencies associated with them. Certainly, in connection with the large stationary machines, the utility of such a machine for any particular patient is limited to the time when the patient can visit and be connected with that machine. Thus, such a machine is incapable of providing continuous treatment of an ambulatory patient. With respect to the smaller portable TENS units, these units do offer the advantage of treatment of an ambulatory paitent, but they likewise are not entirely satisfactory. That is, such units are quite expensive, often costing several hundred dollars, and while a patient with severe or chronic pain might consider such a cost to be worthwhile, the average patient with a minor or temporary pain such as a sprained ankle or muscle pull is unlikely to be willing to make such an investment. Additionally, existing forms of TENS units require placement of and removal of the electrodes, often using electrode gel, at precise locations on the patient's body. The patient must be trained as to where and how to apply the electrodes, how to remove the same, how to recharge the batteries, and other mechanical aspects of the system. Also, the use of wires extending from the unit to the electrodes presents an unsightly appearance, and such patients must therefore use the device in private or suffer the embarassment of being seen in public with wires projecting from the electrodes to the power unit. Also, the patient is able to adjust or alter the stimulation pattern or strength prescribed by the physician, with the possibility that such adjustment could render the device ineffective. Still further, existing forms of TENS units can treat only limited areas of the body since there are only two or four electrodes provided on the unit.

With the foregoing in mind, it is an object of the present invention to overcome the difficulties, deficiencies and shortcomings associated with existing forms of electrical stimulation units, and to provide instead, a new and improved unit in the form of a bandage which is capable of creating pain blocking signals that are transmitted into a person's body to block the pain arising from an injury.

Another object of the present invention is to provide a pain-blocking bandage which is self-contained in that it need not be connected with any external power supply to render it operative.

Another object of the present invention is to provide a pain-blocking bandage which is flexible enough to permit it to conform to an injured portion on a person's body.

Another object of the present invention is to provide a pain-blocking bandage which is light-weight and which can be applied to and carried by a portion of a person's body without undue discomfort.

Another object of the present invention is to provide a pain-blocking bandage which is relatively flat and which has no projecting wires or other protrubrances to be attached to an external source, thereby enabling the bandage to be worn without presenting any unsightly or embarassing appearance.

Another object of the present invention is to provide a pain-blocking bandage which is relatively inexpensive so that it can be applied to a patient's body, used continuously until the electrical energy has been dissipated, and then discarded.

Another object of the present invention is to provide a pain-blocking bandage which can be worn continuously by a patient and which need not be removed for recharging purposes.

Another object of the present invention is to provide a pain-blocking bandage which becomes operative upon application to the patient's body, and which thus needs no special training or skills on the part of the patient in order to receive the beneficial effects of the bandage.

Another object of the present invention is to provide a pain-blocking bandage which includes a pair of separable units to enable one of such units to be easily replaced when it becomes inoperative while the other unit still remains operative.

Another object of the present invention is to provide a pain-blocking bandage which becomes operative upon application to a patient's body and which remains in continuous operation for the effective life of the bandage.

Another object of the present invention is to provide a pain-blocking bandage which can be adjusted or altered electrically by the patient.

Other objects, advantages and salient features of the present invention will become apparent from the following detailed description, which, taken in conjunction with the annexed drawings, discloses preferred embodiments thereof.

The foregoing objects are attained by providing a bandage which is formed of two separate units which are interconnected one on top of the other in actual usage. The first or inner unit which is applied directly onto the patient's body includes a housing or body having separated conductive portions therein, advantageously in the form of a pair of spaced apart openings in the housing, each of which is filled with an electrolyte. The underside of the housing applies directly to the patient's skin.

The second or outer unit of the present invention is removably mounted upon the first unit. The second unit includes spaced electrodes and a means for generating a voltage to such electrodes. Advantageously, this voltage generating means is formed by a power cell connected with an electronic circuit which in turn is connected with the electrodes. In one embodiment of the invention, the electrodes contact directly against the electrolyte in the spaced openings in the inner unit so that the voltage can be transmitted through the electrolyte to the patient's skin. In another embodiment of the invention, a pair of confronting printed circuit boards are used. Both printed circuit boards can be provided on the underside of the outer unit or both printed circuit boards can be provided on the upper surface of the inner unit or one printed circuit board can be mounted on the inner unit and the other on the outer unit. In this embodiment, the confronting circuit boards are provided with electrical coupling means so the voltage can be transmitted across such printed circuit boards and delivered to and through the electrolyte in the inner unit and applied to the patient's skin.

Advantageously, the voltage delivered from the second unit to the first unit, and hence through the first unit to the patient's skin, is a pulsing voltage. Because of the skin resistance of the patient's body, this pulsing voltage creates a pulsing low current in the patient's body, accompanied by a magnetic field force, the effect of which is to block or mask the pain sensations arising from the injury to which the bandage is applied.

The upper and lower memebers are both relatively thin and are both formed advantageously of plastic or other suitable flexible material. As a result, the entire bandage unit is not only self-contained, in that it carries all of the electrical components needed to create the pain-blocking signals, but in addition, is relatively flexible to enable the bandage to conform to that portion of the patient's body which is injured.

Referring now to the drawings, which form a part of this original disclosure.

Before describing the invention in detail, it may be useful to define certain terms used in the application. The term "bandage" is intended to refer to any type of dressing which might be applied over a wound, injury, incision, sprain or other injury. The term "self-contained" means that the bandage is operative as a single unit and need not be connected to any external power supply in order to be operative. The term "constant voltage" as used herein refers to DC voltage. The term "patient" and "person" are used interchangeably to refer to the individual upon whome the bandage is to be used. When it is stated that the bandage is applied "adjacent to" the injured portion, this should be understood to include both application directly upon the injured portion and application near to, but not directly upon, the injured portion. Finally, in referring to the pain treating aspects of the present invention, the terms "block" or "mask" are used interchangeably to refer to the manner of treatment. That is, while the mechanism of operation is not entirely understood, it has been discovered and it is medically recognized that certain pulsing low electrical currents interfere with the transmission of pain signals by the peripheral nervous system and through the central nervous system to the brain. For convenience, this pain interference by these pulsing electric currents is referred to herein as "pain-blocking" or "pain-masking."

Figure 1:
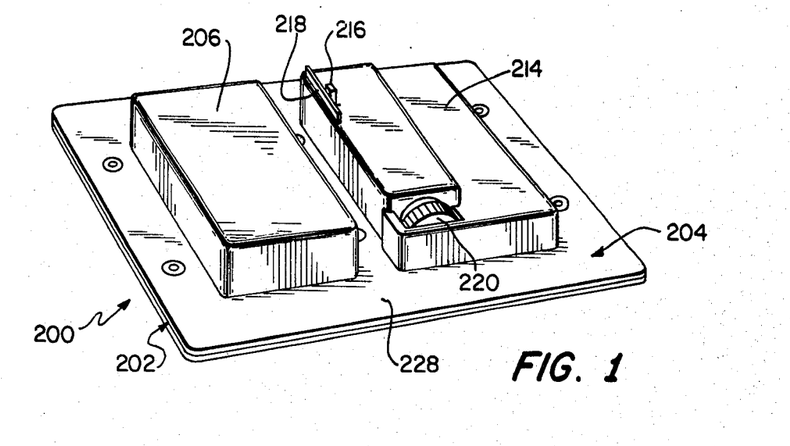
FIG. 1 is a perspective view of an embodiment of a pain-blocking bandage in accordance with the principles of the present invention.

Referring now to FIG. 1, the bandage in accordance with the principles of the present invention is illustrated therein in enlarged form and is generally designated 200. It will be understood that the thickness of the bandage 200 is kept to a minimum, consistent with the various components of the invention which must be included therein, but it can be generally stated that the bandage 200 is relatively thin so that it can be applied to and worn by a patient without creating any large or unsightly bulge. The bandage 200 includes an inner or first unit generally designated 202 which is applied directly to a patient's body and an outer or second unit generally designated 204 which is revovably applied to the first unit 202.

Figure 2:
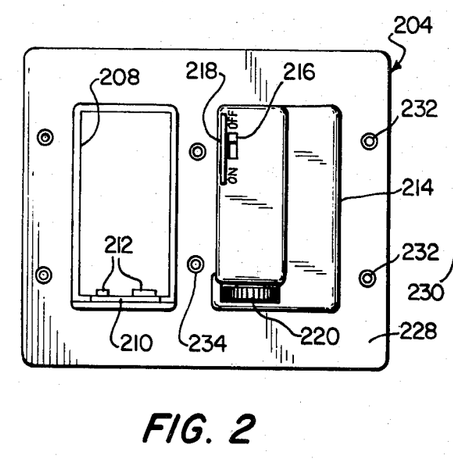
FIG. 2 is a top plan view of an outer unit of the rechargeable type as used in the bandage.
Figure 3:
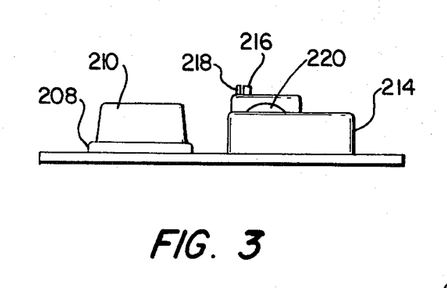
FIG. 3 is a side elevational view of the outer unit.

The outer unit 204 carries a voltage generating means. The voltage supply is in the form of a constant voltage, advantageously from a standard nine volt battery or power cell. In FIG. 1 which shows a disposable unit, the battery is permanently housed within a closed chamber 206. In FIG. 2 which shows a rechargeable unit, the battery is removably housed in an open chamber 208. An upstanding wall 210 at one end of the chamber carries battery terminals 212 to which the battery can be removably attached. Obviously, in the FIG. 2 arrangement, the battery can be removed for recharging. A removable cover, not illustrated, can be used to cover the open chamber 208.

The outer unit 204 also carries, on its upper surface, another closed chamber 214. This chamber 214 houses the electronic circuitry. It includes an on-off switch 216 mounted adjacent to an upstanding wall 218 which prevents accidental movement of the switch 216. It further includes an adjustment wheel or dial 220 which can be digitally operated to vary the magnitude of the electrical output of the unit.

Figure 4:
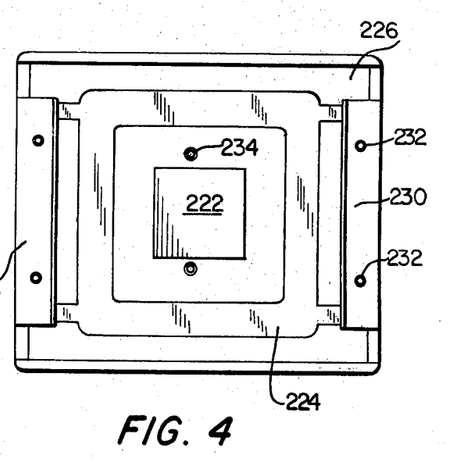
FIG. 4 is a bottom plan view of the outer unit.

FIG. 4 shows the underside of the outer unit 204. On the underside, an inner electrode 222 is positioned centrally and an outer electrode 224 is positioned in concentrically surrounding relationship to the inner electrode. Both electrodes 222 and 224 are mounted upon a thin plastic sheet 226, as more fully shown in FIG. 6. As an advantageous constructional technique, the entire upper surface 228 of the outer unit 204 can be formed of thin, flexible plastic, with the chambers 206 and 214 being preformed therein. The components of the FIG. 1 arrangement, namely, the battery and the circuitry, are placed within the chambers through their open bottoms. Then, the sheet 226, which carries the electrodes which are connected to the circuitry, is positioned beneath the upper surface 228, thereby closing the bottoms of the chambers 206 and 214. Flaps 230, as shown in FIG. 4, fold inwardly across the sheet 228, and rivets 232 pass through the upper surface 228 and flaps 230 to hold the sheet 226 in position. The flaps 230 can be formed integrally with the plastic material forming the upper surface 228. Additionally rivets 234 can be used centrally to further secure the sheet 226 and its attached electrodes.

In the embodiment shown in FIG. 1, where the outer unit 204 is disposable, the electrodes 222 and 224 are simply formed of dissimilar metallic materials, advantageously copper and zinc-plated copper, respectively. In the embodiment shown in FIG. 2, where the outer unit 204 is rechargeable, the electrodes are coated with a conductive rubber material to prevent them from being consumed by the electrical reaction.

Figure 5:
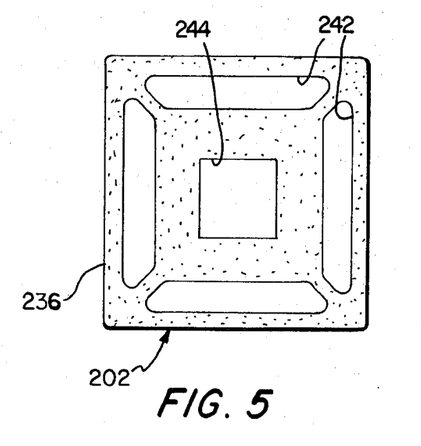
FIG. 5 is a top or bottom plan view of the inner unit as used in the bandage.
Figures 6, 7:
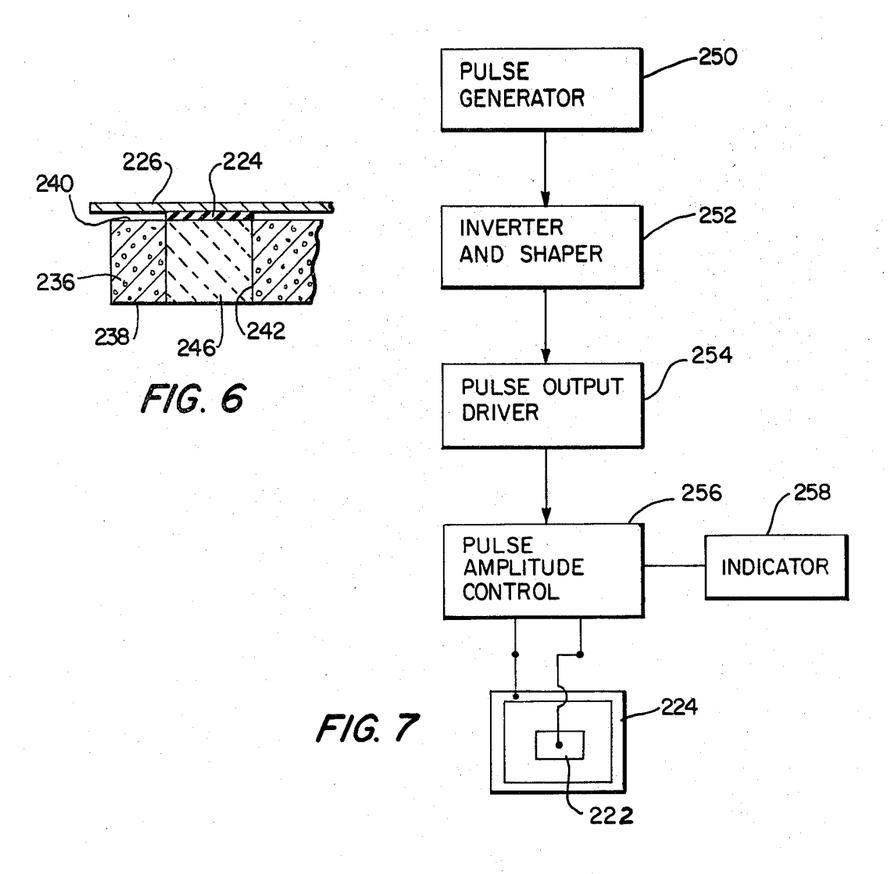
FIG. 6 is an enlarged fragmentary sectional view of a portion of the inner unit and a portion of the outer unit.
FIG. 7 is a block diagram of a circuit arrangement which can be used in the bandage.

The inner or first unit 202 is shown in FIGS. 5 and 6. It includes a housing or body member 236 having a lower surface 238 adapted to be applied directly against the patient's skin and an opposed upper surface 240. A series of outer peripheral openings 242 are provided in the housing 236, extending completely between the lower and upper surfaces 238 and 240. An inner opening 244 is provided centrally in the body member 236, again extending completely between the upper and lower surfaces. As can be seen, the inner opening 244 is completely separated from the outer or peripheral openings 242. Advantageously, the body member 236 is fabricated of foam plastic, silicone, or other suitable material which is both flexible and somewhat compressible.

The arrangement of the openings 242 and 244 in the inner unit body member 236 is such as to coincide with the disposition of the electrodes 224 and 222, respectively, carried by the outer unit. That is, when the second or outer unit 204 is applied upon the first or inner unit 202 in the manner shown in FIG. 1, the inner electrode 222 aligns over the opening 244 and the outer electrode 224 aligns over the openings 242. As can be seen from FIG. 1, the size and configuration of the first and second units 202 and 204 is identical, although the thickness of the units may vary, one from the other. Normally, the inner unit 202 is of a lesser thickness than the outer unit 204.

An electrolyte 246 substantially completely fills the openings 242 and 244 in the inner unit. The electrolyte 246 is either in the form of a gel or a foam, either of which has sufficient viscosity to remain in position within the openings. The electrolyte is polymeric to prevent molecules thereof from being absorbed through the skin. It is also flexible to permit suitable flexing of the bandage 200. Since the specific electrolyte used is not part of the present invention, the composition need not be described in detail. However, it can be stated in general that mixtures of alcohols and salt solutions with gelling agents such as agar, gelations, elluloses, gums, or other suitable substances provide operative electrolytes. Specific forms of electrolyte compositions useful for application to a person's skin include those shown in U.S. Pat. Nos. 4,094,822; 3,989,050; 3,658,726, 3,048,549; and 3,027,333. The electrolyte as contained in the opening 244 forms a first conductive portion in the first or inner unit 202. The electrolyte as contained in the opening 242 forms a second conductive portion, separated from the first conductive portion, in the inner unit 202.

Advantageously, each inner unit 202 can be packaged in a separate foil envelope. Removable plastic film backing sheets can be provided on either side or both sides of the unit. In this manner, a doctor or other practitioner can provide a patient with one outer unit and with several separate inner units, each packaged separately. In use, the patient removes the inner unit 202 and applies it to his or her skin at the prescribed location. The patient then places the outer unit 204 upon the inner unit 202 and turns the switch 216 to its "on" position. The patient then turns the adjustment dial 220 slowly towards a higher setting until a confortable tingling sensation is felt. An audible indicator, to be described hereinafter, can be provided in the circuitry to provide a very low "buzzing" sound when the unit is turned on. Alternatively, the indicator can be a visual one with a blinking signal lamp. The patient maintains the two superimposed units in position by taping the same to his or her skin using a hypo-allergenic tape or by using an elastic bandage.

If reference is made to FIG. 7, there is shown therein a block diagram of a suitable form of electronic circuit to operate the bandage 200. A pulse voltage generator 250 produces an essentially square pulse output at a predetermined frequency. An inverter and shaper 252 inverts the pulses and optimizes the pulses as to width and amplitude. A pulse output driver 254 amplifies the pulses. A pulse amplitude control 256 controls the output amplitude of the pulse train. The indicator 258 merely provides an audible or visual signal that the bandage is operating. If the signal is audible, its loudness increases with the amplitude of the output signal. Finally, as indicated, the pulsed output is transmitted to the electrodes 222 and 224. In turn, the electrodes transmit the signal to and through the conductive electrolyte 246 in the openings 242 and 244 to the patient's body to cause low current electrical pulses within the patient's body to block or mask the pain arising from the injury which the bandage 200 is treating.

Figure 8:
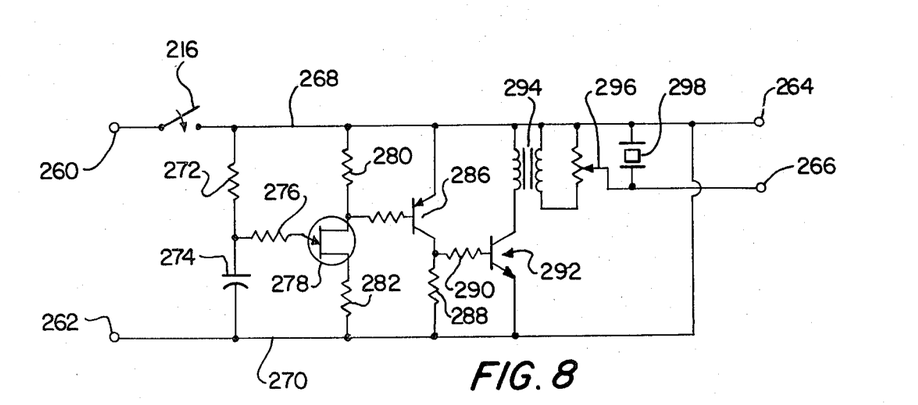
FIG. 8 is a circuit diagram of a circuit in accordance with the block diagram of FIG. 7.

The specific electronic circuit used in the bandage does not form a part of the present invention. However, a suitable form of circuit which accomplishes the objectives of the invention is shown in FIG. 8. The input terminals 260 and 262 connect with the power means or power source, which, as previously mentioned, is advantageously a nine volt battery. The output terminals 264 and 266 connect with the inner and outer electrodes 222 and 224. The on-off switch 216 is used to complete the circuit in its "on" position. The lines 268 and 270 are connected by an RC circuit which includes a resistor 272 and capacitor 274. This RC circuit serves as a time constant circuit to determine the frequency of oscillation of the voltage output. The RC circuit is connected through a resistor 276 with a unijunction transistor 278 having a load resistor 280 from one transistor base to the line 268 and a load resistor 282 from the other transistor base to the line 270. This arrangement provides a unijunction oscillator which forms the pulse generator 250.

The circuit then connects through a resistor 284 with a transistor 286 having one base connected through a load resistor 288 to the line 270 and having the other base connected to the line 268. This arrangement provides the PNP shaper and inverter 252.

The circuit then connects through a resistor 290 to a transistor 292 which forms a Darlington driver. One base of the transistor 292 is connected with the line 270 and the other base is connected with a step-up transformer 294 coupled with the line 268. This forms the pulse output driver 254.

A potentiometer connects with the transformer 294 and adjustably controls the pulse output amplitude. This provides the pulse amplitude control 256. The digitally adjustable dial wheel 220 is used to adjust the potentiometer 296.

Finally, a piezo-electric buzzer 298 is connected between the potentiometer 296 and the line 268 and this arrangement serves as the indicator 258.

Figure 9:
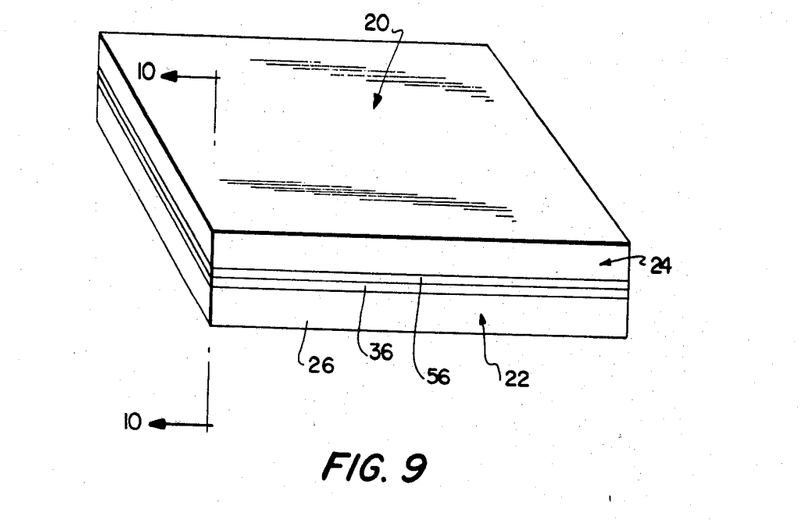
FIG. 9 is a perspective view of another embodiment of a pain-blocking bandage in accordance with the principles of the present invention.

Referring now to another embodiment of the invention as shown in FIG. 9, the bandage therein is generally designated 20. It includes a first or inner unit generally designated 22, analagous to the inner unit 202, and a second or outer unit generally designated 24, analagous to the outer unit 204.

Figure 11:
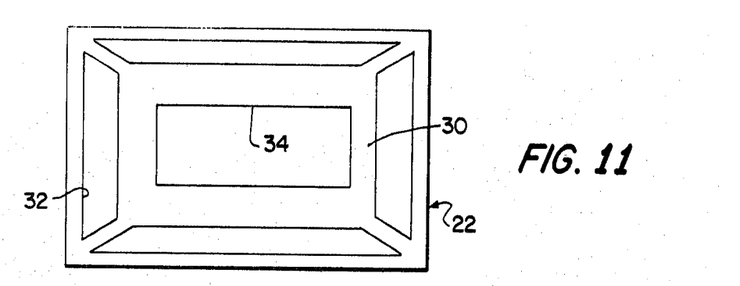
FIG. 11 is a top plan view of the inner unit, looking in the direction of the line 11—11 of FIG. 10.
Figure 12:
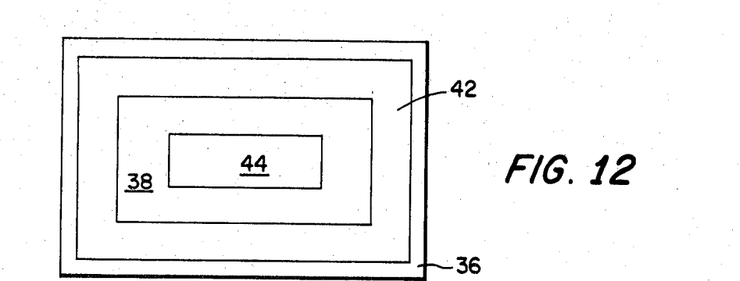
FIG. 12 is a bottom plan view of the first printed circuit board, looking in the direction of the line 12—12 of FIG. 10.

The inner unit 22 includes a housing or body member 26 having a lower surface 28 adapted to be applied directly against the patient's skin and an opposed upper surface 30. As best seen in FIG. 11, a series of outer peripheral openings 32 extend completely through the housing 26 adjacent its periphery and a central opening 34 extends through the housing 26 also.

Figure 13:
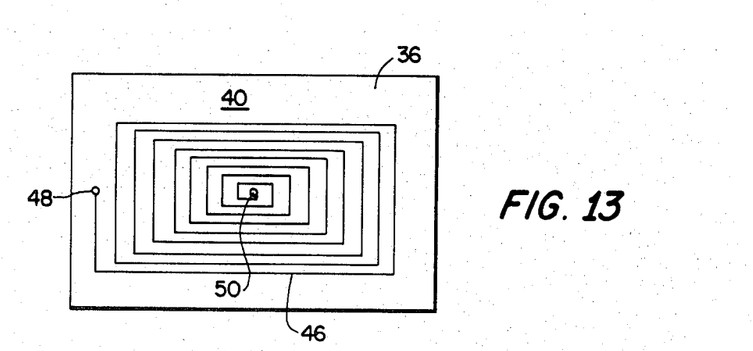
FIG. 13 is a top plan view of the first printed circuit board, looking in the direction of the line 13—13 of FIG. 10.
Figure 14:
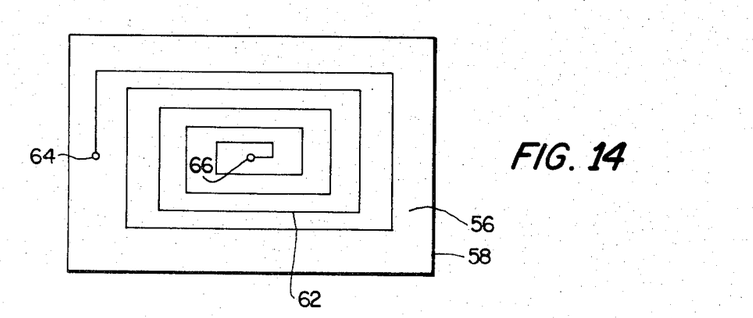
FIG. 14 is a bottom plan view of the second printed circuit board, looking in the direction of the line 14—14 of FIG. 10.

A first printed circuit board 36 is mounted upon the upper surface 30 of the body member. This printed circuit board, as shown in FIGS. 13 and 14, includes a lower or undersurface 38 and a top or upper surface 40. Electrode means are provided on the undersurface 38 of the printed circuit board 36. This electrode means includes an outer electrode 42 aligned to overlie the outer openings 32 and an inner electrode 44 aligned to overlie the inner opening 34. These electrodes are formed of dissimilar metals. Advantageously, the inside electrode 44 is formed of copper while the outside electrode 42 is formed of zinc or chromium plated over copper. On the upper surface 40 of the printed circuit board 36, a coil or spiral 46 is provided. A post or terminal 48 extends through the printed circuit board 36 to connect the outer end of this coil 46 with the outer electrode 42. Another post or terminal 50 extends throug the printed circuit board 36 to connect the inner end of the coil 46 with the electrode 44. As shown, the coil or spiral is formed as a squared spiral in order to get the maximum number of turns. However, any suitable type of would coil or spiral can be used.

The arrangement described thus far forms the lower unit 22. The printed circuit board 36 is attached to the body 26 by a suitable permanent adhesive, preferably extending about the peripheral edges. The only feature of the lower unit not described thus far is the electrolyte 52 which is provided in and which substantially completely fills the openings 32 and 34. The electrolyte 52 is analagous to the electrolyte 246.

Figure 19:
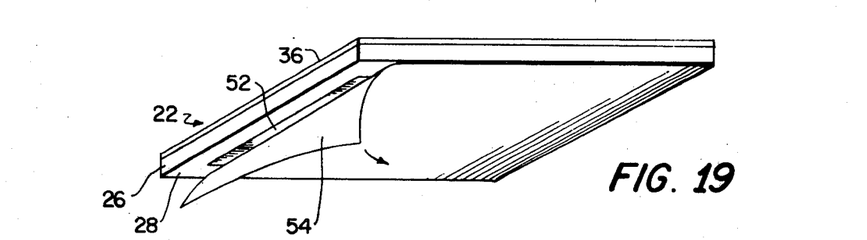
FIG. 19 is a perspective view of the underside of the inner unit, illustrating the manner of removal of the backing sheet.

Before considering the operation of the lower unit 22, attention should be directed to FIG. 19, which shows the lower unit with a removable backing sheet 54 thereon. This backing sheet is advantageously applied across the lower surface 28 of the unit at the time of manufacture and it remains so attached until the unit is ready to be applied to the patient's skin. In this manner, the electrolyte 52 is maintained sterile. When the doctor or medical technician decides to apply the unit 22 to the patient's skin, he or she simply grasps the backing sheet 54 and peels the same away, as illustrated by the arrow in FIG. 11. Similar backing sheets can be provided on one or both sides of the inner unit 202.

Considering the operation of the lower unit 22, that unit generates a substantially constant voltage when it is placed in a position where the electrolyte 52 contacts the patient's skin. Advantageously, the patient's skin is previously abraded by means of a small brush or eraser or similar instrument which removes the dead skin surface and thereby lowers the skin resistance. Alternatively, the patient's skin is pre-wetted with a conductive solution to lower skin resistance. Because the skin is electrically conductive even though it has a certain electrical resistance, there is an electrical flow from the positive electrode 44, through the electrolyte in the opening 34, through the patient's skin to the electrolyte in the outer openings 32, back up to the negative electrode 42, through the terminal 48, the coil 46 and the terminal 50 to return to the electrode 44, where it thereupon repeats the cycle. This voltage flow is created by the differing electrochemical activity of the metals forming the electrode 44 and electrode 42 of the unit. Since the zinc forming the electrode 42 is more reactive than the copper which forms the electrode 44, there is an ionic reaction which displaces copper ions, thus creating an oxidation-reduction transfer of electrons which sets up the electrical flow. As the electrochemical action continues, a portion of the electrodes become consumed in the reaction thereby generating a certain heat of reaction. In addition, there is a tendency for the aqueous portion of the electrolyte 52 to be repelled by the electropositive electrode and attracted by the electronegative electrode. This combination of heat of reaction and aqueous repulsion will eventually cause the electrolyte 52 to dry out at the anode, and, when that occurs, the electrical flow terminates. On units which have been constructed and tested, it has been found that the lower units 22 are operative for approximately 48 hours. While the magnitude of the voltage will obviously vary depending upon sizes, materials and the like, it has been found that units 22 can be expected to generate a substantially constant 0.8 volts during their period of operation.

Figure 15:
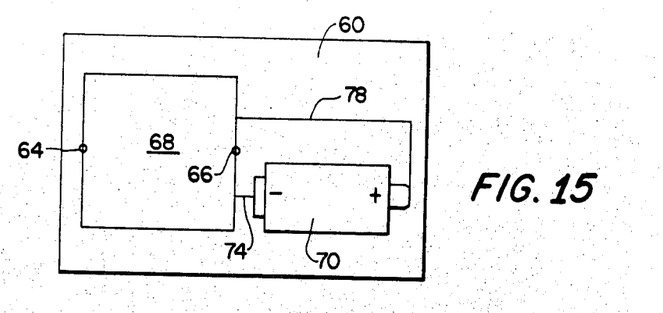
FIG. 15 is a bottom plan view of the outer unit, looking in the direction of the line 15—15 of FIG. 10.

Referring now to FIGS. 14 and 15, there is illustrated therein the second or outer unit 24 which includes the second printed circuit board designated 56. The second printed circuit board has a lower surface 58 which is directed toward the upper surface 40 on the first printed circuit board. It also includes an upper surface 60 on the opposite side thereof. On the lower surface 58, there is provided another wound coil 62, again shown as a squared spiral. This coil 62 is similar to the coil 46, but has less windings. As will be explained, this enables the coils 46 and 62 to coact as a transformer, and the differential in windings permits the transformer to function as a step-up transformer.

Figure 21:
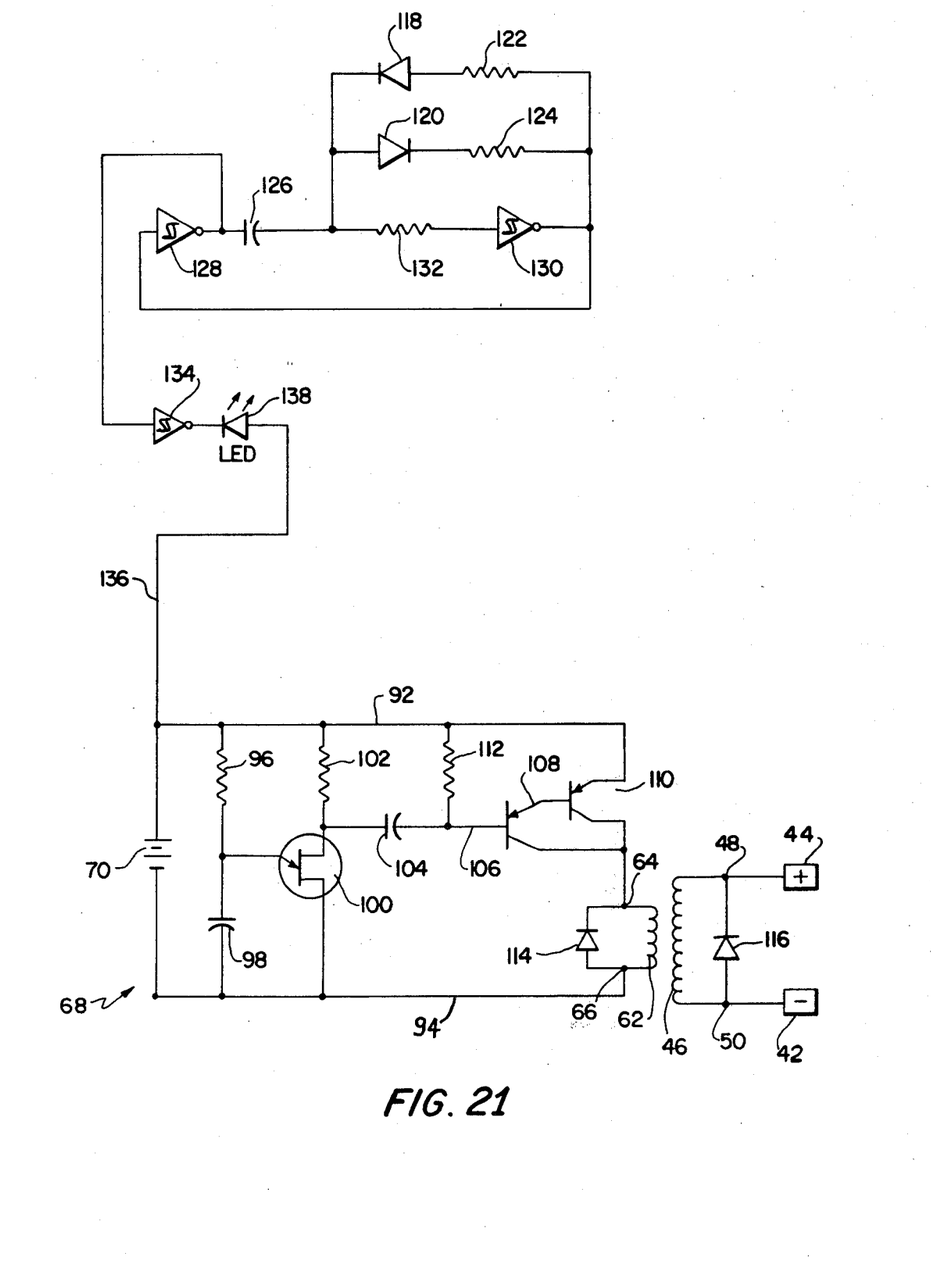
FIG. 21 is a circuit diagram of a circuit which can be used in the bandage.

Terminals or posts 64 and 66 are connected to the outer and inner ends of the coil 62, respectively, and extend through the printed circuit board 60 to connect to an electronic circuit 68 which is provided at the upper surface 60 of the printed circuit board. In FIG. 15, this electronic circuit 68 is merely shown in a block diagram form, but a suitable detailed circuit will be described hereinafter in detail and is shown in FIG. 21. The upper surface of the printed circuit board 56 also carries at least one power source means 70 which provides direct current voltage to the electronic circuit 68.

Figure 10:
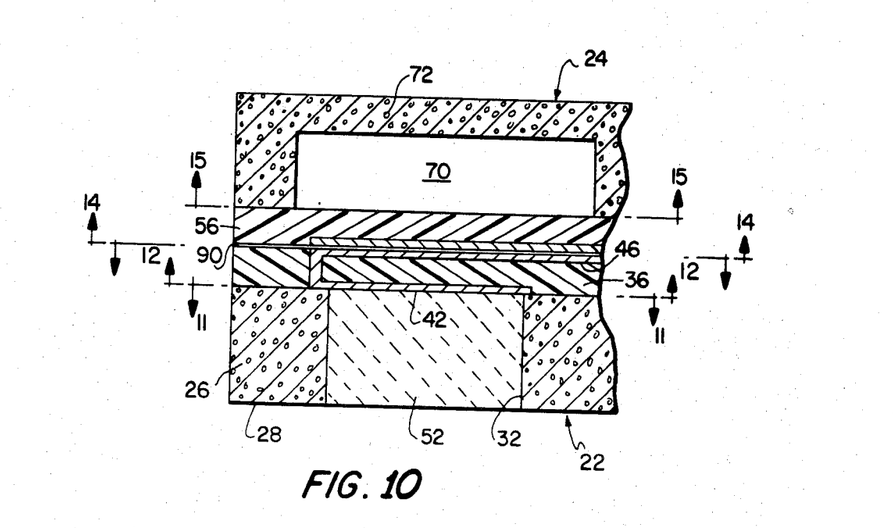
FIG. 10 is an enlarged fragmentary sectional view taken along the line 10—10 of FIG. 9.

Finally, as perhaps best illustrated in FIG. 10, the entire upper unit 24 is formed as a housing 72, advantageously of the same material as the housing 26, and it serves to embed and encapsulate the electronic circuit 68 and the power source means 70. Thus, all components above the upper surface 60 of the second printed circuit board are embedded within the housing 72.

Figure 16:
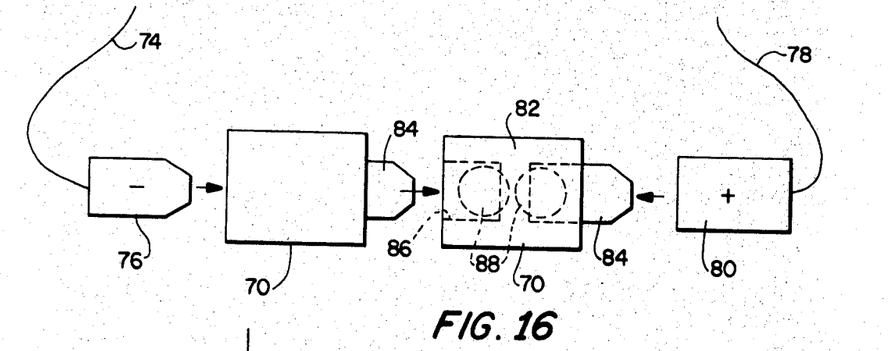
FIG. 16 is a diagrammatic view showing power cells which can be used in the present invention and the manner of connecting the same to an electronic circuit.

As illustrated in FIG. 15, and in more detail in FIG. 16, two leads from the electronic circuit 68 are provided to connect the electronic circuit with the power source means 70. One lead 74 carries on its end a male member 76 adapted for insertion into the power source means 70 and which serves as the negative terminal or connection. Another lead 78 carries on its end a female connector 80 which serves as the positive connector or terminal and is likewise adapted for attachment to the power source means 70 at its opposite end.

The power source means 70 are designed for interconnection with one another by a plug-in type connection which thereby connects the power cells in series. Specifically, it will be noted that on each power source means, there is a housing 82 having a projecting terminal or male member 84 at one end thereof and a socket or female opening 86 at the opposite end thereof, the socket 86 being designed for reception of the male member 84. In this manner, as illustrated in FIG. 16, the power sources can be interconnected together simply by plugging the male end of one into the female socket of the next adjacent one. Power for each power source is provided by means of a pair of small flat watch batteries 88 which are mounted within the housing 82 and electrically connected to both the male member 84 and socket 86. As a result, when only a single power source 70 is used, as illustrated in FIG. 15, that power source is connected to the electronic circuit 68 by insertion of the negative connector 76 into the socket 86 and by connection of the positive connector 80 to the male projection 84. For bandages of smaller sizes, e.g., less than three inches square, only a single power source means 70 need be provided and the two batteries 88 give a three volt output. On the other hand, for larger size bandages, two or more power source means are interconnected together in the manner illustrated by the arrows in FIG. 16. With two interconnected power sources, the output will be six volts, with three, the output will be nine volts, and so on.

If attention is now directed to FIG. 21, there is illustrated therein a electronic circuit 68 which can be used in conjunction with the bandages of this embodiment of the invention. In this circuit, it can be seen that the coils 46 and 62, namely, the confronting coils from the two printed circuit boards, coact to form an inductive electrical coupling means or transformer. When mutual inductance exists between coils in separate circuits, these circuits are considered to be inductively coupled. The effect of the mutual inductance is to transfer energy from one circuit to the other by transformer action. That is, the current flowing in one circuit as a result of a voltage applied to that circuit produces a magnetic flux which induces a voltage in the coupled circuit, thereby resulting in a transfer of energy from the first or primary circuit to the coupled or secondary circuit. When two coils, like coils 46 and 62, are inductively coupled, they constitute the equivalent of a transformer. In practice, as shown in FIG. 10, a very thin non-conductive film 90, which can even be a sprayed film, is positioned between the two coils to prevent them from shorting against one another.

Figure 17:
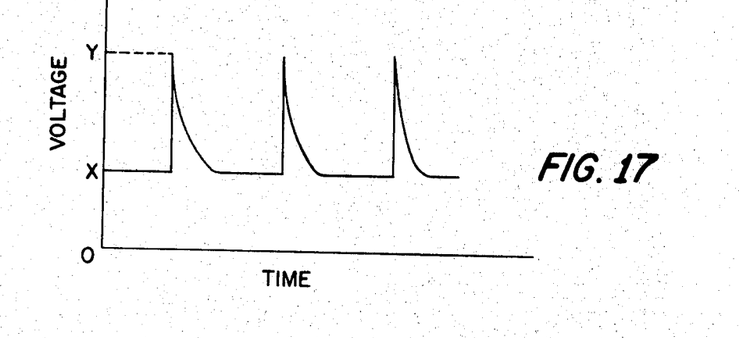
FIG. 17 is an illustration of the waveform of the resultant pulsing current generated in the patient's body.

In FIG. 21, the power means 70 is connected to leads 92 and 94 which connect the power cell to the primary winding or coil 62. An RC circuit including a resistor 96 and capacitor 98 is connected across the lines 92 and 94. This RC circuit serves as a time constant circuit to determine the frequency of oscillation of the voltage output. The RC circuit is connected with a unijunction transistor 100 which in turn has a load resistor 102 connected between the line 92 and one transistor base. A coupling capacitor 104 is connected by a lead 106 to a pair of transistors 108, 110, connected in a Darlington configuration. A bias resistor 112 connects between the line 106 and the line 92. This resistor 112 provides transistor bias as well as a discharge path for the coupled circuits. The two transistors 108 and 110 serve as a current amplifier and not only provide current to the primary coil 62, but, in addition, serve as a buffer to prevent loading of the unijunction transistor 100. A free-wheeling diode 114 is connected across the primary winding 62 to prevent inductive kick-back voltages from destroying the Darlington arrangement. On the secondary side of the circuit, a rectifying diode 116 is provided to remove any negative pulses. Operationally, the unijunction transistor 100 creates a series of voltage spikes as illustrated in FIG. 17. These spikes have a very sharp rise time and a relatively sharp decay time, as shown. Because of the arrangement of the primary and secondary coils 62 and 46, the resultant transformer is of a step-up type which provides an increase in the amplitude of the voltage delivered to the secondary 46. If the arrangement is reversed, so that coil 62 has more windings, the resultant transformer is of a step-down type which produces an increase in current in the secondary coil.

The bandage of this embodiment of the present invention uses a flashing signal light which operates when the bandage is activated by placing the same in contact with the patient's skin. The actual placement of the tiny signal lamp is not shown, since this can be varied as a matter of aesthetics. However, the circuit diagram of FIG. 21 includes a separate signal light circuit. This separate circuit is needed because the normal operational frequency of voltage spikes from the transistor 100 is relatively rapid, e.g., one hundred pulses per second, and that frequency is too rapid for visual observation of the blinking or flashing effect of the light.

The separate circuit for the light, shown at the top of FIG. 21, includes a pair of steering diodes 118, 120, each of which is connected with a load resistor 122, 124, respectively, to control the charge and discharge of a timing capacitor 126 which, in turn, determines the frequency of flashing of the light. A pair of Schmitt triggers are connected on opposite sides of the timing capacitor 126. These Schmitt triggers are ultra-high speed switching devices. A high resistance isolating resistor 132 is connected between the triggers 128, 130. Another Schmitt trigger 134 is connected along a line 136 which connects the lamp circuit to the lower voltage circuit. A light emitting diode 138, which forms the blinking signal light, is likewise provided in line with the trigger 134.

Figure 18:
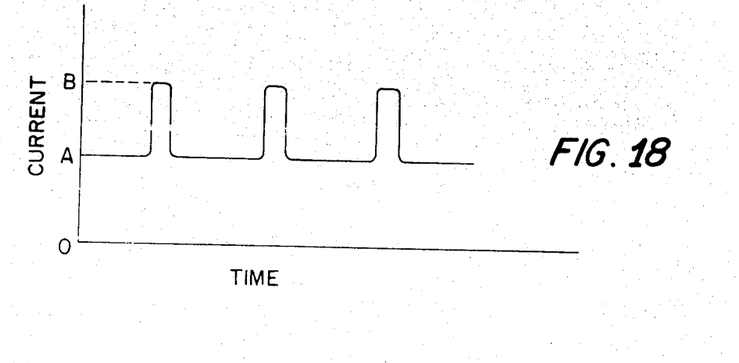

FIG. 17 illustrates the resultant voltage output from the bandage of the present invention. The lower unit 22, as previously described, generates a substantially constant current which is designated X in FIG. 17. The voltage spikes or pulses from the circuit 68 are superimposed or added upon the constant voltage X from the lower unit, thereby creating a waveform as illustrated in FIG. 17. The magnitude of these spikes is shown as Y. Thus, the waveform shown in FIG. 17 can be considered to be the resultant pulsing voltage being generated by the entire bandage and being transmitted through the electrolyte and to the patient's skin. Because of the inherent resistance of the patient's skin, the resultant pulsing voltage is converted within the patient's body into a pulsing current. The general waveform of this current is illustrated in FIG. 18. As can be seen, the current maintains a lower value of A but periodically rises to a higher lelvel B where it remains for a short interval of time before returning to level A. It will be noted that both the rise time and the decay time of the current are very rapid thus creating a pulsing current wave of the form illustrated in FIG. 18.

As examples of the mangitude of values attendant to bandages of this embodiment of the present invention, and without in any way trying to limit the present invention to such values, it can be stated that a typical value of X in FIG. 17 might be 0.8 volts and a typical value of Y in FIG. 17 might be 1.8 volts, which means that 1 volt spikes are being superimposed upon a 0.8 volt constant voltage. The frequency of the spikes is about 100 pulses per second. These figures would hold true for a bandage of relatively small size, e.g., a 1.5"×1.5" bandage. On a larger bandage, e.g., 3"×4" or 4"×6", the value of Y in FIG. 17 could be 9.8 volts meaning that 9 volt spikes are being superimposed upon a constant 0.8 volts. In connection with FIG. 18, a typical value of A might be 100 microamps and a typical value of B might be 200 microamps, meaning that within the patient's body, there is a constant 100 microamp current being delivered with frequent pulses raising that value to 200 microamps. All of the empirical values are by necessity calculated with the ultimate pulsing current values in mind. That is, it is recognized that above a level of 300 to 400 microamps, there is a discomfort or pain index for most patients. Accordingly, the bandages are designed to keep the values well within patient tolerance levels and at the present time it is believed that a range of 10 to 100 microamps is the most effective for the combination of patient comfort and the requisite pain-blocking function.

Figure 20:
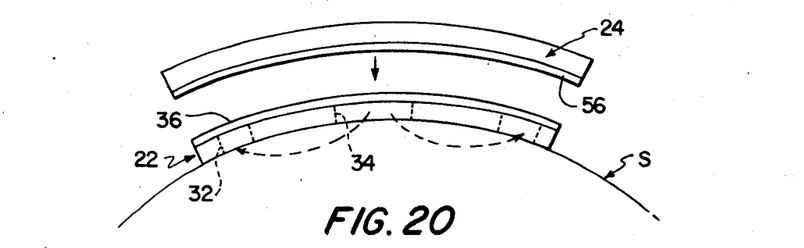
FIG. 20 is a diagrammatic view showing the inner unit as applied against a patient's body and the outer unit about to be applied upon the inner unit.

As previously indicated, the inner units 22 might be expected to have a useful life of approximately 48 hours or two days. On the other hand, the outer units 24 have a considerably longer life span, e.g., ten days. As a result, the doctor or technician who provides the bandage units to the patient might provide one upper unit 24 and five lower units 22 which would then permit ten days of continuous pain-relieving treatment of a patient's injury. All of the components of the bandage 20 are normally interconnected with each other by means of suitable peripheral adhesives, but if the lower units 22 are to be continually replaced, some other form of attachment means, for example, an overwrap, may be used. Thus, in reference to FIG. 20, there is illustrated the lower unit 22 applied directly against the patient's skin S. The electrical flow path from that lower unit is demonstrated by the arrows. After the lower unit is prepared for application, for example, by exposing the pressure sensitive adhesive surrounding the peripheral edge of the lower surface 28 by removal of the backing sheet 54, the lower unit is then properly situated on the patient's body covering the injury or injured portion. The upper unit 24 is then activated, plated above, and brought down into contact with, the lower unit. Some means must be provided to keep the upper unit from being activated while it is in storage, or else the power source means 70 would become depleted prior to use. One simple way to accomplish this is by placing a plastic strip adjacent the power cells 88 to keep them from making contact until the strip is pulled out to activate the circuit. As previously indicated, a nonconductive film 90 should be placed between the two units to prevent shorting of the coils against one another. This film 90 can be applied by a simple aerosol spray across the upper surface 38 of the printed circuit board 36. The upper unit 24 is then placed into contact with the lower unit and is retained in place by means of adhesive tape, a flexible overwrap such as an elastic bandage, or any other suitable means.

Figure 22:
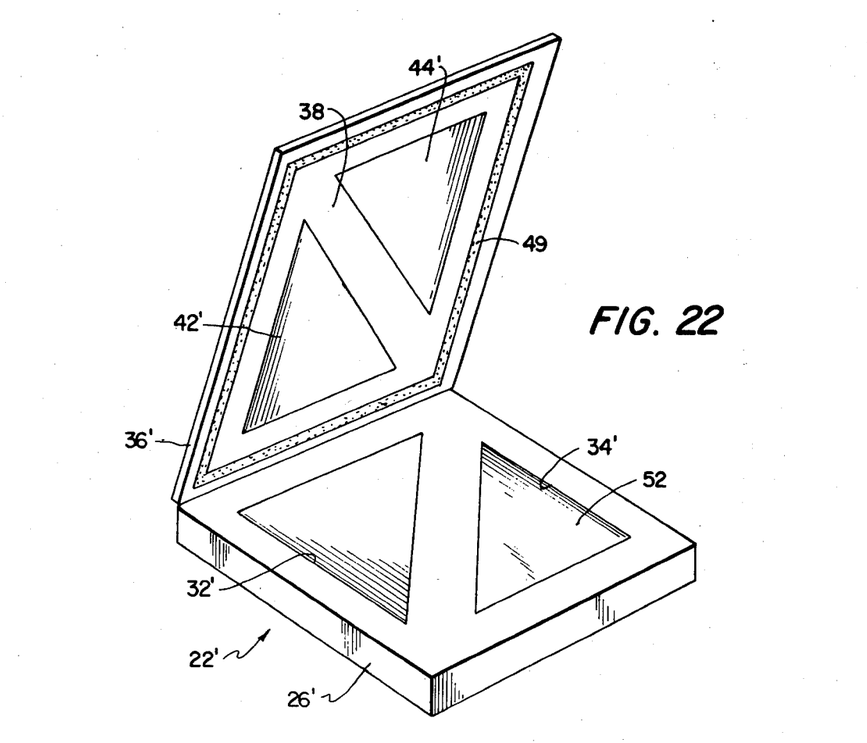
FIG. 22 is a diagrammatic perspective view showing a modified form of the inner unit and a modified form of first printed circuit board.

If attention is directed to FIG. 22, there is shown therein a modified form of lower unit 22'. It includes a body portion 26' which has a pair of triangular openings 32' and 34' of substantially equal size and shape, diagonally separated from one another. The electrolyte 52 fills both openings in the body 26'. As a result, when the printed circuit board 36' is applied over the body 26', and maintained in position by suitable adhesive such as that peripherally arranged in FIG. 22 and illustrated as 49, the printed circuit board will be attached to the body portion to form the modified lower unit, and in such modified lower unit, the positive and negative electrodes will each be aligned over an opening which contains the electrolyte. This type of configuration is advantageously used on the smaller sizes of bandages.

Figures 23, 24, 25:
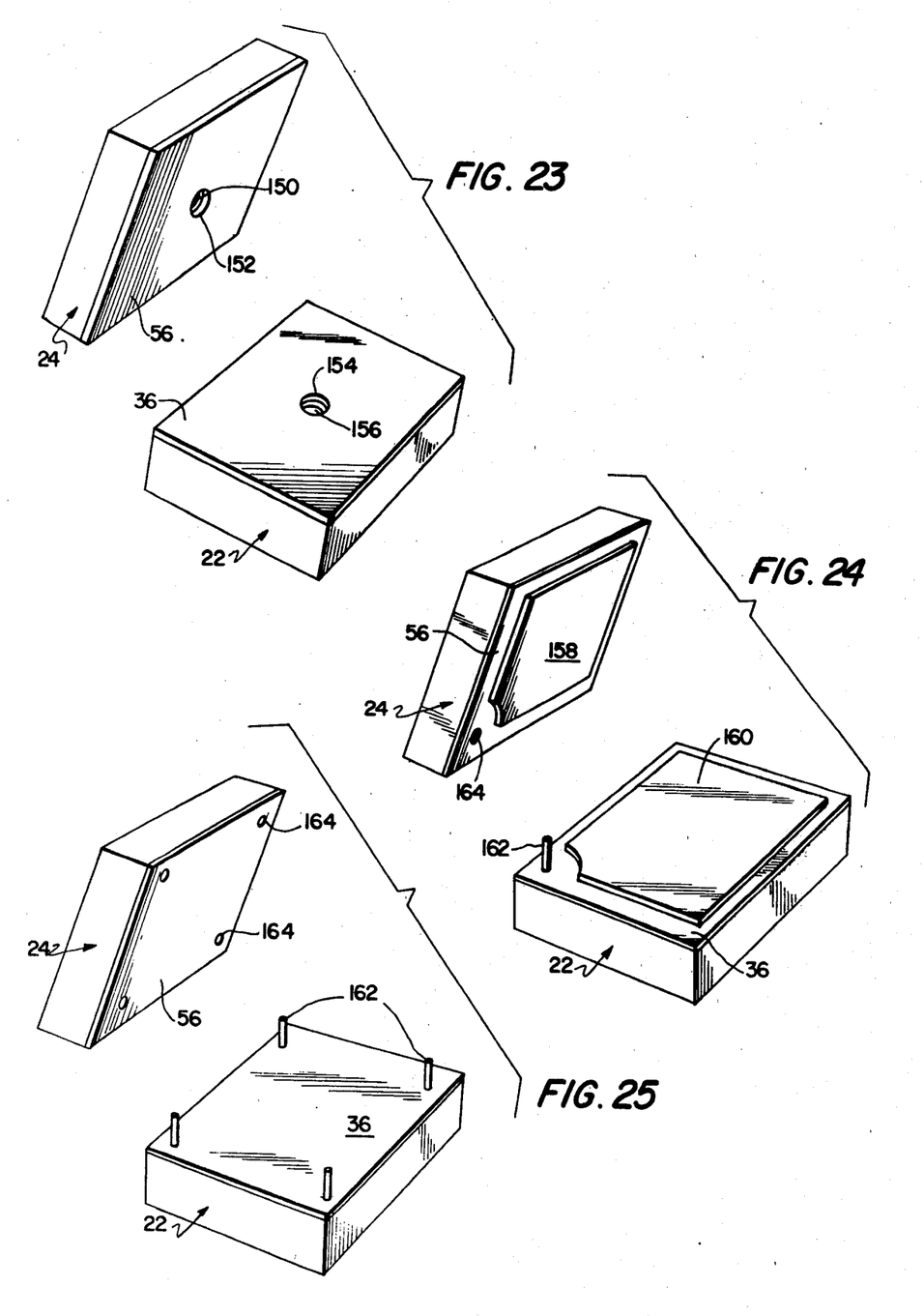
FIG. 23 is a simplified perspective view of an opto-electronic coupled circuit arrangement.
FIG. 24 is a simplified perspective view of a capacitive coupled circuit arrangement.
FIG. 25 is a simplified perspective view of a direct coupled circuit arrangement.

While the bandage thus far described for the FIGS. 9–22 embodiments uses inductively coupled circuits, created by the separate but confronting coils 46 and 62, this invention clearly comprehends the use of other types of coupled circuits. Any two electrical circuits are considered to be coupled if energy can be transferred electrically or magnetically from one to the other. Since this embodiment of the present invention involves two circuits, advantageously provided with one in the lower unit 22 and one in the upper unit 24, the coupling of these circuits permits energy transfer between them for accomplishing the beneficial effects of the present invention. FIGS. 23, 24 and 25 illustrate, respectively, opto-electronic, capacitive and direct coupled circuits, all of which can be used in lieu of the inductive coupled circuit heretofore described.

FIG. 23 illustrates the opto-electronic or optical coupling arrangement. In such arrangement, a light emitting device 150, such as a light emitting diode, is provided in the upper unit 24, to provide a light pulse through an opening 152 in the printed circuit board 56. An aligned opening 154 in the printed circuit boad 36 overlies a light activated device 156 in the lower unit 22. The coupling is accomplished by impingement of light pulses from 150 onto 156.

FIG. 24 illustrates a capacitive coupling arrangement. A first capacitor plate 158 printed circuit board 56 and an opposed second capacitor plate 160 is etched onto the upper surface of the printed circuit board 36. These capacitor plates are advantageously coated with an insulating wax film. A connector 162 on the lower unit 22 fits into a receptacle 164 on the upper unit 24 to provide a common line.

Finally, in FIG. 25, a direct circuit coupling arrangement is illustrated. In this arrangement, a series of upstanding connector pins 162 on the lower unit 22 fit into a corresponding series of corresponding receptacle holes 164 on the upper unit 24. This enables direct current electrical energy from the lower unit 22 to travel through the pins 62 into the upper unit, combine with the electrical energy from the upper unit, and thereby permit the combined or coupled electrical energy to be delivered to the patient's skin.

It is within the clear purview of this invention to use differing sizes, shapes and thicknesses of materials, to use different materials, to use different electrode arrangements, printed circuit layouts, a variety of different electrolytes, opening sizes, configurations and the like. In short, various changes and modifications apparent to those skilled in the art may be without departing from the spirit and scope of the invention as defined in the appended claims.

What is claimed is:

1. A flexible self-contained bandage adapted to be applied adjacent to an injured portion of a patient's body, said bandage comprising:
   a first unit adapted to be applied to the patient's body;
   a second unit removably applied upon said first unit;
   said second unit including means for generating and applying a voltage output to said first unit;
   said first unit having separated conductive portions;
   said voltage output being transmitted through said conductive portions to the patient's body to cause low current electrical pulses within the patient's body to block or mask the pain arising from the injury.

2. A bandage as defined in claim 1 wherein said first unit includes a container with separated openings formed therein and an electrolyte disposed in said openings to form said conductive portions.

3. A bandage as defined in claim 2 wherein said means for generating and applying a voltage output to said first unit includes first and second electrodes which contact against the electrolyte in said openings when said second unit is applied upon said first unit.

4. A bandage as defined in claim 3 wherein said means for generating and applying a voltage output to said first unit includes a power cell and a circuit, said power cell being electrically connected with said circuit and said circuit being electrically connected with said first and second electrodes.

5. A bandage as defined in claim 4 wherein said power cell is removable and rechargeable.

6. A bandage as defined in claim 4 further including adjustment means connected with said circuit to permit digital adjustment of the magnitude of the voltage output to said first unit.

7. A bandage as defined in claim 6 further including digitally operable switch means which in one position interrupts the electrical connection between said power cell and said circuit to thereby deactivate the bandage and which in another position establishes the electrical connection between said power cell and said circuit to thereby activate the bandage.

8. A bandage as defined in claim 7 further including signal means connected with said circuit to provide a signal when said bandage is activated.

9. A bandage as defined in claim 8 wherein said signal means provides an audible signal.

10. A bandage as defined in claim 8 wherein said signal means provides a visual signal.

11. A bandage as defined in claim 4 wherein said second unit includes
   a member having an underside and an upper side; and
   a cover overlying said upper side;
   said first and second electrodes being attached to the underside of said member;

said power cell and said circuit being positioned between said upper side of said member and said cover.

12. A bandage as defined in claim 11 wherein said first and second electrodes are formed of dissimilar metals whereby an electrolytic reaction occurs as said voltage passes through said electrolyte; said reaction providing an added voltage component which is transmitted to the patient's body.

13. A bandage as defined in claim 1 wherein said means for generating and applying a voltage output to said first unit comprises circuit means which generates a pulsing voltage superimposed upon a constant voltage with the resultant voltage being applied to said first unit.

14. A bandage as defined in claim 13 wherein said first unit includes a container with separated openings formed therein and an electrolyte disposed in said openings to form said conductive portions.

15. A bandage as defined in claim 14 wherein said means for generating and applying a voltage output to said first unit includes first and second electrodes which contact against the electrolyte in said openings when said second unit is applied upon said first unit.

16. A bandage as defined in claim 15 wherein said means for generating and applying a voltage output to said first unit includes a power cell electrically connected with said circuit means, and wherein said circuit means is electrically connected with said first and second electrodes.

17. A bandage as defined in claim 16 wherein said power cell is removable and rechargeable.

18. A bandage as defined in claim 16 further including adjustment means connected with said circuit means to permit digital adjustment of the magnitude of the voltage output to said first unit.

19. A bandage as defined in claim 18 further including digitally operable switch means which in one position interrupts the electrical connection between said power cell and said circuit means to thereby deactivate the bandage and which in another position establishes the electrical connection between said power cell and said circuit means to thereby activate the bandage.

20. A bandage as defined in claim 19 further including signal means connected with said circuit means to provide a signal when said bandage is activated.

21. A bandage as defined in claim 20 wherein said signal means provides an audible signal.

22. A bandage as defined in claim 20 wherein said signal means provides a visual signal.

23. A bandage as defined in claim 16 wherein said second unit includes
a member having an underside and an upper side; and
a cover overlying said upper side;
said first and second electrodes being attached to the underside of said member;
said power cell and said circuit means being positioned between said upper side of said member and said cover.

24. A bandage as defined in claim 23 wherein said first and second electrodes are formed of dissimilar metals whereby an electrolytic reaction occurs as said voltage passes through said electrolyte; said reaction providing said constant voltage.

25. A bandage as defined in claim 1 wherein said means for generating and applying a voltage output to said first unit includes a first voltage producing circuit means which generates a constant voltage and a second voltage producing circuit means which generates a pulsing voltage which is superimposed upon said constant voltage.

26. A bandage as defined in claim 25 wherein said first and second voltage producing circuit means are electrically coupled.

27. A bandage as defined in claim 26 wherein said circuit means are inductively coupled.

28. A bandage as defined in claim 27 wherein said inductive coupling is provided by a primary coil attached to one of said circuit means and a secondary coil attached to the other of said circuit means, said coils being arranged in confronting arrangement with one another.

29. A bandage as defined in claim 26 wherein said circuit means are directly coupled.

30. A bandage as defined in claim 26 wherein said circuit means are capacitively coupled.

31. A bandage as defined in claim 26 wherein said circuit means are opto-electronically coupled.

* * * * *